United States Patent [19]

Castor et al.

[11] 4,139,497

[45] Feb. 13, 1979

[54] DEHYDROGENATION CATALYST TABLET AND METHOD FOR MAKING SAME

[75] Inventors: William M. Castor, Clute; Pete J. Menegos, Lake Jackson, both of Tex.

[73] Assignee: The Dow Chemical Company, Midland, Mich.

[21] Appl. No.: 784,480

[22] Filed: Apr. 4, 1977

[51] Int. Cl.$^2$ .................. B01J 23/78; B01J 23/86; B01J 35/02

[52] U.S. Cl. .................. 252/470; 252/477 R; 260/669 R

[58] Field of Search .................. 252/470, 477 R; 260/669 R; 264/13, 15

[56] References Cited

U.S. PATENT DOCUMENTS

| | | | |
|---|---|---|---|
| 3,209,049 | 9/1965 | Pitzer | 252/470 X |
| 3,849,339 | 11/1974 | Turley et al. | 252/470 X |

OTHER PUBLICATIONS

Abstract BE-843,682, Central Patents Index, p. 59, Week Y04, (3/16/77).

Volz, "Spary Drying and Customized Catalyst", Chem. Eng. Progress, vol. 70, No, 11, p. 80 (Nov. 1974).

Primary Examiner—W. J. Shine
Attorney, Agent, or Firm—M. W. Barrow

[57] ABSTRACT

Non-supported, fixed bed catalyst tablets made by spray drying a slurry of the components into microspheres followed by tabletting the microspheres under high pressure in apparatus such as punch and die sets. The catalysts formed according to the process of this invention have better catalytic performance and/or crush strength than do conventionally made pellets such as extrudates.

13 Claims, No Drawings

DEHYDROGENATION CATALYST TABLET AND METHOD FOR MAKING SAME

BACKGROUND OF THE INVENTION

Non-supported, fixed bed catalyst pellets are used in many chemical processes. Among these are processes for dehydrogenation, hydrogenation, and oxidation of organics. Dehydrogenation processes using such fixed bed, non-supported catalysts include the dehydrogenation of ethylbenzene to produce styrene, of ethyl toluene to produce vinyl toluene, and of butane or butene to produce butadiene.

Hydrogenation processes which use such fixed bed, non-supported catalysts include such processes as that for producing saturated hydrocarbons from olefins.

Oxidation processes which use such fixed bed, non-supported catalyst pellets include such processes as those for making aldehydes and acids from saturated and unsaturated hydrocarbons, e.g. acrylic acid from propylene.

For the sake of conciseness, the word pellets is hereinafter used as a generic term to include those spray dried tablets made by the process of this invention as well as other forms of pellets made by such processes as extrusion, i.e., extrudates. Tablet is defined to be any pellet made by the process of this invention.

In the past, improvements in the catalytic performance and/or crush strength of non-supported catalyst pellets for the processes referred to above, have generally been obtained by changing the formulation of components. Typically such non-supported catalyst pellets are made by extruding a paste of components through cylindrical dies to form moist cylinders having a diameter of from about 1/16 inch to about ¼ inch. As these cylinders exit from the extruder they are usually either chopped into predetermined lengths or allowed to break of their own weight, forming cylindrical pellets (extrudates) having a length of from about ⅛ inch to about one inch.

Methods other than extrusion have been taught for forming non-supported catalyst pellets. For example U.S. Pat. No. 1,680,807 (Aug. 14, 1928) teaches the formation of catalyst tablets by compression of a multiplicity of fine particles of catalytic material, which particles are not naturally coherent in the dry state. Spray drying of fluid bed catalysts is known. See U.S. Pat. Nos. 2,768,145 (Tongue et al. 1956) and 1,680,807 (Scultze 1928). Spray drying catalyst materials on catalyst carriers or supports is known. See U.S. Pat. No. 2,435,379 (Archibald 1948).

The process of the present invention, however, comprises the combination of the steps of (1) spray drying a slurry of catalyst source constituents into microspheres, and (2) forming at least one tablet from these microspheres by subjecting them to large compressive forces, such as tabletting in a punch and die set. For some unknown reason this combination of steps produces a catalyst tablet having superior catalytic performance and/or crush strength qualities.

It should be noted that the phrase "a slurry of catalyst source constituents" is used above in the spray drying step as opposed to "a slurry of catalyst components". This is done to point out that sometimes the constituents used in making up the slurry for spray drying are not the same components as those found in the final formulation of the catalyst tablets to be used. Often after adding the constituents together, or in subsequent steps in making the catalyst pellets, chemical changes occur in these constituents. Thus different constituents other than those started with often appear in the final catalyst pellet formulation. Of course, there are also catalyst slurry formulations which are not changed. This invention is applicable to both. Hence, as used hereinafter the phrase "catalyst source constituents" is defined to mean not only those constituents which appear in one form in the slurry and another form in the finished catalyst tablet, but also to those constituents that appear in the same form in both the slurry and the finished tablet. For example $K_2CO_3$ is a source for $K_2O$ if the $K_2CO_3$ is converted to $K_2O$. Also $K_2O$ itself is source of $K_2O$ by this definition.

SUMMARY OF THE INVENTION

This invention relates to a new method for making a fixed bed, non-supported catalyst tablet having either improved catalytic performance qualities, or improved crush strength, or both. The tablet made by this new process is useful in those organic chemical processes involving the use of fixed bed, non-supported catalyst tablets. Such organic chemical processes include dehydrogenation, hydrogenation, and oxidation processes.

The method for making such a fixed bed, non-supported catalyst tablet comprises:

a. forming microspheres by spray drying a slurry containing catalyst source constituents; and b. forming the tablet by compressing a selected amount of the microspheres to a compressive pressure of at least 3,000 psi.

In many applications the catalyst tablets must be further treated to be useful. For example dehydrogenation catalyst tablets often must be calcined, while oxidation catalyst tablets often must be heated in the presence of hydrogen or a hydrogen source.

The method of making these tablets has found use in making fixed bed, non-supported, dehydrogenation catalyst tablets for use in the known process of dehydrogenation of alkyl aromatics, e.g. those aromatics having alkyl groups containing from two to eight carbon atoms, and particularly dehydrogenation of ethylbenzene to styrene. This process comprises passing at an elevated temperature, ethylbenzene mixed with steam over catalyst tablets, said catalyst tablets containing at least oxides of iron, potassium and chromium.

It should be understood that this invention relates also to the catalyst tablets made by the above described process.

DETAILED DESCRIPTION OF THE INVENTION

To specifically illustrate the process by which these new catalyst tablets are made as well as the unexpected improvement in catalytic performance and crush strength of the tablets made by this process, the discussion and examples given below will be in terms of a catalyst tabletting process, and the tablets made by this process, which are used in the dehydrogenation of ethylbenzene to produce styrene monomer.

Typically styrene monomer is made in a dehydrogenation reactor by passing ethylbenzene and steam at an elevated temperature through a bed of catalyst pellets. These pellets are comprised of oxides of iron, potassium and chromium.

In the past these pellets have usually been formed by a process comprising;

a. forming a paste comprised of water, lubricant, binders and catalyst source constituents of the oxides of iron, potassium, and chromium;

b. extruding the paste into cylindrical pellets having a diameter of from about ⅛ inch to about 3/16 inch and a length of from about ⅛ inch to about ¾ inch; and c. calcining the pellets at a temperature of from about 500° C. to about 1200° C.

Producing catalyst tablets utilizing the method of this invention can be accomplished by:

A. forming a slurry capable of being spray dried comprised of water and catalyst source constitutents of oxides of iron, potassium and chromium;

B. spray drying the slurry into microspheres;

C. forming a catalyst tablet from a selected amount of the spray dried microspheres by compressing the microspheres; and D. calcining the tablet at a temperature of at least 500° C.

These steps will now be elaborated upon in the following discussion.

A. SLURRY FORMATION

In forming a slurry suitable for spray drying, any method can be used which gets the catalyst formation components into an aqueous solution, aqueous suspension, or both.

The amount of water present in the slurry is not a critical limitation. Rather, this amount depends on the operating capabilities of the particular spray dryer used. A slurry containing from about 20 wt.% to about 70 wt.% water is found satisfactory for nearly all spray dryers. A range of about 40 wt.% to about 60 wt.% water is preferable for most disk type spray dryers.

The oxides of iron, chromium, and potassium which are found to be necessary in the final catalyst tablet can be, and often are, provided in other chemical forms in the slurry. These other chemical forms, however, must be convertible to the oxides during the remainder of the process of making the tablets. The calcining step is usually the step in which these other forms of iron, potassium, and chromium are converted to the oxides, $Fe_2O_3$, $Cr_2O_3$, and $K_2O$. For example the following equations illustrate other chemical forms from which these oxides can be derived during the calcining step.

$$K_2CO_3 \rightarrow K_2O + CO_2$$

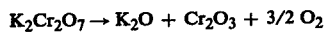
$$K_2Cr_2O_7 \rightarrow K_2O + Cr_2O_3 + 3/2\ O_2$$

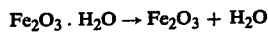
$$Fe_2O_3 \cdot H_2O \rightarrow Fe_2O_3 + H_2O$$

It is immaterial in what form the elements of iron, potassium, chromium, and oxygen occur in the slurry preparation step so long as they can be changed to the oxides themselves in the finished catalyst tablet.

In preparing pellets by the old method of extrusion (i.e., preparing extrudates), it is known that the water-insoluble constituents of the slurry should be ground or otherwise turned into powdered particles. Usually this powder is available commercially. The same water-insoluble powdered ingredients used in the process of producing extrudates are used in the process of this invention. For the comparative runs given below, for each diameter pellet of each formulation, the ingredients used were from the same source. This was done so that there would be no variation in the test results due to variations in the source materials.

B. SPRAY DRYING

Spray drying is a process long known as a process for producing very small, discontinuous, spherical particles from a slurry feed; that is, spray drying produces microspheres usually having a diameter no greater than about 500–1,000 microns for most formulations from most spray dryers. For a general description of spray dryers and their operation, see *Perry's Chemical Engineers' Handbook*, John H. Perry, editor, Third Edition, McGraw-Hill Book Co., Inc., New York, Toronto, and London, pages 838–848 (1950), incorporated herein by reference.

Spray dryers are classified into three general categories, centrifugal disk, pressure nozzles, and two-fluid nozzles. Any of these are suitable for use in the process of this invention, but the disk type is preferred for large scale commercial operations.

Neither the moisture content nor the particle size distribution of the microspheres made by the spray drying step of this invention are critical limitations. Of course, there are practical limitations that the particular spray dryer being used imposes upon these two parameters, and, of course, the microspheres' diameters should not be of the same order of magnitude as the finished non-supported catalyst tablets desired to be produced.

Having the diameter of the spray dried microspheres approach the size of the finished tablets poses no problem generally. This is so because the diameter or size of the smallest tablet contemplated by this invention is on the order of about 1/16 inch while the largest microspheres usually produced by commercial spray dryers are on the order of only about 500–1000 microns. This size microsphere is within the operable limits for making the tablets contemplated by this invention. Insofar as the diameter of the microspheres is concerned, it was found that better catalytic performance of the catalyst tablets was achieved when the diameter of about 80% of the microspheres was greater than about 20 microns. It is preferable to have a particle size distribution of the spray dried microspheres such that about 80% of the microspheres have diameters which lie in a range of from about 20 microns to about 200 microns, and more preferable if this range is from about 20 microns to about 100 microns. Smaller microspheres caused the equipment used in the tabletting step to bind and exhibit extreme wear. The larger sizes caused no perceptible problems.

Variations in moisture content of the spray dried microspheres, as noted above, was not found to be critical in so far as the catalytic performance of the finished tablets were concerned. Moisture content of the microspheres had more of an effect on the operation of the particular spray dryer and auxillary equipment used. A moisture content of from about zero weight percent to about 5.0 wt.% produced catalytic tablets which were satisfactory in their catalytic performance and crush strength as well as for operation of the equipment. Large moisture contents caused poor flow properties.

C. COMPRESSION INTO TABLETS

After spray drying the slurry into microspheres, the next step in the process of this invention is to form relatively large tablets from these microspheres by subjecting predetermined amounts of these microspheres to a compressive pressure. This compressive pressure is not critical, but should be great enough to produce tablets having sufficient crush strength to withstand the physical loads and attrition to which they will ultimately be subjected. Usually such compressive pressures are best achieved in punch and die equipment.

As a general rule, the greater the tabletting pressure used, the greater will be the crush strength of the tablets. Tablets with adequate strength were made using a compressive tabletting pressure as low as about 3,000 psi. Generally, however, it is preferred to use a compressive pressure of greater than about 15,000 psi and even more preferred to use a compressive pressure of at least about 22,000 psi. It is more preferred to use a compressive pressure of from about 22,000 psi to about 45,000 psi, and most preferable to use a compressive pressure of from about 28,000 psi to 38,000 psi. The higher pressures of these latter two pressure ranges are chosen as a compromise between acceptable tablet crush strengths and catalytic performance and the pressure operating limits of the equipment used. No upper limit was found for the compressive pressure, however. Compressive pressures greater than about 130,000 psi were used in a laboratory test run which produced very good tablets, but known commercial equipment was not available for large scale manufacture of tablets made with this large a pressure.

Subjection of the spray dried material to large compressive pressures (greater than from about 3,000–15,000 psi) is herein also referred to as "tabletting". The pellets formed by such tabletting is herein also referred to as "tablets" to distinguish them from those pellets formed by extrusion, herein also referred to as extrudates.

Note that "pellets" can be and is used herein, to denote tablets made by the process of this invention as well as to denote extrudates made by the known extrusion process. It is clear, however, from the context in which "pellets" is used, whether tablets, extrudates, or both is intended.

In the tabletting step of the process, the molds or dies are chosen with shapes such that the tablets formed will have the desired size and shape.

The most preferred shape for fixed bed, non-supported catalyst pellets produced by any method is spherical. Adequate dies to produce such spherical shapes, however, were not readily available at the time this invention was reduced to practice. Thus no examples are shown for making spherical shaped fixed bed self-supporting catalyst tablets. This shape, however, is certainly within the scope of this invention as are other non-cylindrical shaped pellets, such as ellipsoids, cubes, star shapes, frustroconical shapes, hollow cylinders, and the like.

Generally cylindrically shaped tablets are easier to make. Cylinders with convex ends are preferable. There is no critical size limit for these tablets. Catalytic performance tends to fall off as the diameter of the tablets varies from about 3/16 inch in the styrene reactors tested. The diameter of these cylindrical tablets can be from about 1/16 inch to about one inch. Preferably the diameter is from about ⅛ inch to about ½ inch, with a more preferred diameter being from about ⅛ inch to ¼ inch. The most preferred diameter is 3/16 inch. The length of the cylinders can be from about 1/16 inch up to about one inch. It has been found, however, that less attrition and mechanical breakage of the tablets occur if the tablets are made so that their length is approximately the same as their diameter. This latter shape approaches the most preferred tablet shape, spheroids.

D. CALCINING

Following the compressison of the microspheres to form tablets, these tablets are usually calcined. Typically calcining is carried out at a temperature of from about 500° C. to about 1200° C. for a time of from about one or two to about 20 hours. Calcining can be carried out in a special calcining chamber or in the reactor itself. This calcining step for the tablets formed by the method of this invention is carried out in virtually the same manner as has heretofor been done for the calcining of extrudates. This is well known to those of ordinary skill in the art of making extrudates for use in dehydrogenating ethylbenzene to produce styrene.

EXAMPLES OF MAKING SPRAY DRIED TABLETS BY THE METHOD OF THIS INVENTION

A slurry was made as follows: To 1,411 gal. of water were added the following water soluble solid constituents in the amounts given: 5,600 lbs. of $K_2CO_3.3/2H_2O$, 839.5 lbs. of $K_2Cr_2O_7$, and 839.5 lbs. of $V_2O_5$. To this solution was added the following water insoluble solid components in powdered form in the amounts given and in particle size distribution given: 14,573 lbs. of $Fe_2O_3$ powdered particles ranging in size from about 3 microns to about 49 microns, 5,883 lbs. of $Fe_2O_3.H_2O$ powdered particles ranging in size from about 2 microns to about 52 microns, 869 lbs. of Portland cement ranging in size from about 2 microns to 55 microns, 4,278 lbs. of METHOCEL*, powdered particles, ranging in size from about 3 microns to about 250 microns; and 4,145 lbs. of graphite powdered particles ranging in size from about 1 micron to about 13 microns.

*METHOCEL is a registered trademark of The Dow Chemical Company denoting a particular brand of methyl cellulose.

Additional water was added to the above slurry so there was a solids to water ratio of 0.94:1 in the resulting slurry.

This suspension was then fed as the feed to the feed inlet pump of a centrifugal rotating disk type spray dryer at a temperature of 30° C. The spray dryer is referred to as the Standard AA Spray Machine by its manufacturer, Bowen Engineering, Inc., whose principal manufacturing site is Sommerville, New Jersey. The model used had the following features. It had an atomizing disk wheel which was 5 inches in diameter. This disk wheel was located near the top of the drying chamber of the spray drier. This drying chamber was conical in shape being supported in an upright position with the larger portion above the smaller portion. Its largest diameter was 7 feet and its height was 12 feet. The flow of the drying air was cocurrent to the downward falling of the microspheric particles.

The rate of the feed to the atomizer disk was 0.77 gallons/minute. The disk was rotated at a speed of 21,600 R.P.M. The inlet temperature of the drying air was 260° C. while its outlet temperature was 149° C.

The dried microspheres were exhausted from the spray drying chamber of the spray dryer into its bag filter collector. The microspheres were observed to be both of the ruptured surface and smooth surface type. They had a particle size distribution of from 5 microns to about 27 microns diameter with moisture of less than 1 wt.%.

The microspheres were then fed to a tabletting machine. This machine is referred to as a Model #900-565-1 Stokes Ultra Press by its manufacturer, the Stokes Division of Pennwalt Corp. of Warminster, Pennsylvania. In the tabletting machine, the microspheres were fed into 0.200 inch inside diameter dies and were compressed with punches at a pressure of 36,400 psi.

The tablets produced by the tabletting machine were cylindrical in shape. They were 0.210 inches in diameter and 0.180 to 0.290 inches long. They had an average crush strength of 29 lbs. as measured by a Pfizer hardness tester instrument.

The tablets were then calcined in a kiln at temperatures ranging from 683° C. low to 732° C. high with an average temperature of 703° C. for a time of about 1 to 1.5 hours. Following calcination, the tablets were observed to have an average relative crush strength of 27 lbs. measured by the same Pfizer instrument used above to measure the uncalcined tablets.

The calcined tablets were than analyzed and found to contain $Fe_2O_3$ - 70.2 wt.%; $K_2O$ - 4.6 wt.%; $K_2CO_3$ - 10.6 wt.%; $Cr_2O_3$ - 2.8 wt.%; $V_2O_5$ - 4.0 wt.%; cement - 3.3 wt.%; carbon - 4.3 wt.%.

COMPARATIVE EXAMPLES

Eighteen experimental runs were made so that nine pair of comparisions could be made between the catalytic performance and crush strength of catalyst tablets made by the method of the present invention and the catalytic performance and crush strength of catalyst extrudates made by conventional extrusion.

In each pair of comparative runs made, the catalyst pellets (tablets and extrudates) were made from the same formulation and had the same diameter. Three different formulations were used. Three different diameters for the catalyst pellets were used for each formulation. Two different methods of pellet preparation were used for each diameter. The comparisons made are between those pairs of runs in Table II whose catalyst pellets were made from the same formulation and have the same diameter.

In all of these comparative runs, the hydrocarbon dehydrogenated was ethyl benzene (EB) and the specific product looked for was styrene monomer. Data are assembled in Table II.

The three different formulations used are well-known, useful, dehydrogenation catalysts. The particular constituents of these formulations and their weight ratios (excluding free water) are given in Table I. These specific formulations are herein referred to as F-1, F-2, and F-3.

reactor produces greater conversion of the ethylbenzene to styrene. Thus a compromise has been utilized in the past between using a smaller catalyst pellet, which has greater catalytic activity, and using a larger catalyst pellet which allows a lower operating pressure.

With the present invention such a compromise still has to be made, but with the discovery of this invention, larger catalyst pellets can be used without encountering as great a loss in catalytic activity and crush strength as was experienced before when using conventionally made pellets such as extrudates.

In the comparative examples below pellet crush strength was determined on an average value of 20 pellets (tablets and extrudates) from each of the eighteen batches of pellets made using a Pfizer Hardness Tester instrument. This instrument gives a reading proportional to the total force, in units of pounds force, which it takes to cause these pellets to crumble.

The two different methods of catalyst preparation used for each diameter of each formulation were (1) the conventional method of extruding a paste into pellet extrudates and then calcining the extrudates; and (2) spray drying a slurry containing the catalyst constituents, sufficiently compressing the microspheres in a tabletting machine to form tablets of the same diameters and formulations as the extrudates, and then calcining the tablets. A detailed elaboration of these two methods for preparing the catalyst extrudates and tablets is given following Table II.

The extrudates and tabletted pellets prepared for each diameter of each formulation were tested for performance in mini-reactors. The reactor used for both the ⅛ inch and 3/16 inch extrudates and spray dried tablets was a part of a 35 inch long, 1 inch diameter, 316 stainless steel pipe. The reactor used for the ¼ inch diameter extrudates and spray dried tablets required a 1.5 inch diameter pipe. Otherwise the mini-reactors were the same.

The pipes for both of these mini-reactors were erected upright. Both reactors were fitted with a beaded wire heater and heater control means to control the temperature in their reactor zones. Both reactors were well insulated. In every comparison run, whether in the 1 inch or 1.5 inch diameter reactors, the catalyst pellets, whether extrudates or spray dried tablets, were installed in the mini-reactors to form a catalyst bed seven inches high. Beneath the catalyst bed, but still in the pipe, eleven inches of spacers was installed to support the catalyst pellets. Above the catalyst bed, but still

TABLE I

| Catalyst | Slurry Formulations (wt. Percent) | | | | | | | | |
|---|---|---|---|---|---|---|---|---|---|
| | $Fe_2O_3$ | $Fe_2O_3 \cdot H_2O$ | $K_2CO_3 \cdot 3/2\ H_2O$ | $K_2Cr_2O_7$ | $Cr_2O_3$ | $V_2O_5$ | Cement | METHOCEL* | Graphite |
| F-1 | 79.7 | — | 18.0 | — | 2.3 | — | — | — | — |
| F-2 | 50.6 | 12.6 | 17.9 | 2.7 | — | 2.7 | 3.0 | 8.9 | 1.6 |
| F-3 | 9.6 | 64.4 | 20.5 | 2.2 | — | — | 3.3 | — | — |

*METHOCEL is a registered trademark of The Dow Chemical Company denoting a particular brand of methyl cellulose.

The three different pellet diameters chosen for testing each formulation were ⅛ inch, 3/16 inch, and ¼ inch. In the past conventional catalyst pellet diameters have ranged from about ⅛ inch to about ¼ inch. It is known that smaller diameter pellets are normally more active and have greater crush strength than larger ones. Larger diameter pellets have the advantage of producing less pressure drop in the reactor. Lower pressure drop within a styrene monomer reactor allows the absolute pressure within the reactor to be lower than it would be otherwise. And lower absolute pressure in a in the pipe, a 17 inch section of the pipe used as a preheater and mixing zone. This zone contained porcelain Berl saddles, a well known type of column packing used in distillation columns.

The preheater section also had a beaded wire heater wrapped around it as did the heater for the reactor section of the pipe described above.

Into this preheater there was fed 99% pure ethylbenzene (EB) and water. As the EB and water fed through the preheater stage they were heated to a temperature approaching reaction temperature. This temperature is above the vapor forming phase of the EB and the water. The Berl saddles and boiling action of the EB and water caused the EB and water to become a well mixed vapor mixture. In this vapor state the mixture entered the reactor zone of the pipe in which were located the catalyst pellets (extrudates or tablets).

The liquid hour space velocity (LHSV)* of the EB-steam mixture was maintained at 1.0 vol./vol./hour. The weight ratio of the steam used to the EB used was maintained at 2.0:1.
*LHSV is defined as the volume flow of fluid per hour divided by the volume of catalyst present.

For each batch of pellets tested, the operating temperature for the reactor was kept constant for each of the runs of a particular formulation; i.e., all the F-1 formulation runs were made at 575° C., the F-2 runs at 610° C. and the F-3 runs at 600° C.

The measured catalytic performance, i.e., conversion of ethylbenzene to styrene, for these runs is shown in Table II.

The small particles of water insoluble constituents of the formulation being used were then added to the solution of soluble constituents of that formulation and thoroughly mixed to form a slurry having about 75 wt.% solid material. This solid material percentage is calculated by considering both the soluble and insoluble material as solid.

Next the resulting mixed slurries were dried in an oven at about 110° C. until the free water content of each mixture was down to about 10 to 12 wt.% so that a paste was formed.

The paste for each formulation and each of the three diameters used, ⅛", 3/16" and ½", was then extruded using a pellet mill commonly used for such purposes manufactured by The California Pellet Mill Company of San Francisco, California.

The extrudates formed by this pellet mill varied in length from about ⅛ inch to about ½ inch for each of the three diameter pellet extrudates produced, with the

TABLE II

Comparative Runs Made at Constant Temperatures for Each Formulation

| Run No. | Formulation[1] | Pellet Diameter " | Type of Pellet | Average Crush Strength (lbs) | Operating Temp. (° C) | % Conv. of EB to Styrene |
|---|---|---|---|---|---|---|
| 1 | F-1 | 1/8" | EX[2] | 19 | 575 | 38.86 |
| 2 | F-1 | 1/8" | SDT[3] | 37 | 575 | 48.82 |
| 3 | F-1 | 3/16" | EX | 13 | 575 | 40.30 |
| 4 | F-1 | 3/16" | SDT | 35 | 575 | 41.14 |
| 5 | F-1 | 1/2" | EX | 37 | 575 | 9.13 |
| 6 | F-1 | 1/2" | SDT | 37 | 575 | 17.24 |
| 7 | F-2 | 1/8" | EX | 20 | 610 | 57.49 |
| 8 | F-2 | 1/8" | SDT | 20 | 610 | 61.24 |
| 9 | F-2 | 3/16" | EX | 16 | 610 | 50.39 |
| 10 | F-2 | 3/16" | SDT | 30 | 610 | 57.49 |
| 11 | F-2 | 1/2" | EX | 36 | 610 | 29.32 |
| 12 | F-2 | 1/2" | SDT | 36 | 610 | 35.64 |
| 13 | F-3 | 1/8" | EX | 21 | 600 | 55.38 |
| 14 | F-3 | 1/8" | SDT | 21 | 600 | 58.40 |
| 15 | F-3 | 3/16" | EX | 6 | 600 | 50.89 |
| 16 | F-3 | 3/16" | SDT | 16 | 600 | 56.44 |
| 17 | F-3 | 1/2" | EX | 15 | 600 | 33.13 |
| 18 | F-3 | 1/2" | SDT | 15 | 600 | 38.24 |

[1]See Table I for formulation specifics of F-1, F-2, and F-3.
[2]EX stands for extrudate; i.e. pellets made by conventional catalyst extrusion methods.
[3]SDT stands for spray dried tablet; i.e. tablets made by the method of this invention.

From Table II it can be seen that the catalyst performance and catalyst crush strength of the spray dried tablets prepared by the method of this invention was as good or better than that of the conventionally made extrudates for a given formulation and a given diameter. Specifically in Table II it can be seen that in every case the tablet made by the method of this invention converted more ethyl benzene to styrene monomer than the conventionally made extrudates made from the same formulation and having the same diameter. It can be seen that the crush strength of the spray dried tablet made by the process of this invention is as good or better than the conventionally made extrudates.

PREPARATION OF THE TABLETS AND EXTRUDATES FOR THE COMPARATIVE RUNS SHOWN IN TABLE II

Extrudate Pellets

The extrudate pellets of the three formulations used were made by the conventional extrusion method. This method is as follows.

First the soluble components going into making the extrudates for each particular batch were dissolved in water. The insoluble components were in powder form and were thoroughly mixed.

The soluble constituents of the formulations in Table I are $K_2CO_3 \cdot 3/2 H_2O$, $K_2Cr_2O_7$, and $V_2O_5$.

larger diameter pellets tending to have the longer lengths. These lengths were formed as the continuous extrusions of paste exiting from the pellet die was cut by a knife.

The pellet extrudates were then calcined at a temperature of about 700–900° C. for 3 hours.

Spray Dried Tablets Preparation for Comparative Runs

The different batches of spray dried tablets made for the comparative runs of Table II were made by first forming the constituents of the particular formulation into a water slurry in the same way the mixture used to form the paste for the conventional extrudate pellets above was made. Thus, the water soluble constituents were added to water and this solution was thoroughly mixed with the insoluble components obtained from the same source from which the insoluble constituents were obtained. The slurry contained about 35 wt.% solid material. The weight percent of the solid material of the slurry was calculated as including the water soluble as well as the water insoluble constituents.

The slurry was fed to a laboratory disk type spray drier manufactured by Anhydro, Inc. of North Attleboro, Massachussetts. In this spray drier the slurry was led from a reservoir to the top of the atomizer wherein it was passed down a feed tube to an atomizer wheel. The slurry entered the interior of the wheel and because of the high rotational speed of the wheel (40,000 rpm), it was flung outward at a high rate of speed in droplet form. These droplets produced a very fine, uniform mist. This mist entered the drying chamber of the atomizer from the periphery of the atomizer wheel. The atomizer wheel had a diameter of 63 millimeters. The drying air at the drying chamber inlet was maintained at 210° C. The outlet temperature in the cyclone filter was maintained at 90° C. The feed rate to the atomizer was maintained at about 1000 grams/hour. The spray dried microspheres produced for all the comparative runs using spray dried tablets contained about 2% moisture. Their diameters ranged from about ten microns to about fifty microns with most of the microspheres having a diameter close to thirty microns. Under an electron microscope some of these microspheres appeared to be of the hollow ruptured type.

These microspheres were then fed to a manually operated Parr Pellet Press manufactured by Parr Instrument Co. of Moline, Illinois. In this press, dies were used which had the same inside diameter as that diameter desired for the tablets to be formed, i.e., ⅛ inch, 3/16 inch, and ½ inch. The dies used were filled with the spray dried microspheres. Sufficient amounts of microspheres were used in the dies so that the length of the tablets formed was substantially the same as was their diameter. The tablets were cylindrical in shape with ends which were slightly rounded.

It was determined that the operator of this press, or tabletting machine, was exerting a fairly constant force on the microspheres in the die through the punch point for all three diameters of the three formulations formed into spray dried tablets for these comparative examples. This force was from about 705 lbs. to about 1,650 lbs. For the ⅛" diameter tablets, this force translates into a compressive pressure of from about 58,750 psi to about 137,500 psi. For the 3/16" diameter tablets, this force translates into a compressive pressure of from about 25,500 psi to about 59,800 psi. For the ½" diameter tablets, this force translates into a compressive pressure of from about 3600 psi to about 8420 psi.

After exerting this pressure on the microspheres, they formed a solid tablet having the dimensions and shape of the cylindrical dies used.

Following the tableting of the spray dried microsphere the formed tablets were then calcined in the same way as were the conventionally made extrudates above; i.e., these spray dried tablets were heated at a temperature of about 700° C. to about 900° C. for about 3 hours.

The crush strength of these spray dried tablets used in Table II were measured following the calcining of the spray dried tablets.

We claim:

1. A method for making an improved fixed-bed, dehydrogenation catalyst tablet which comprises:

a. forming microspheres from a slurry of catalyst source constituents of the oxides of iron, potassium, and chromium by spray drying a slurry containing these catalyst source constituents;

b. forming a catalyst tablet by subjecting a preselected amount of the microspheres to a compressive pressure of at least 3,000 psi; and c. calcining the tablet at a temperature of at least 500° C.

2. The catalyst tablet made by the process of claim 1.

3. A catalyst tablet for use in the dehydrogenation of ethylbenzene to styrene made by the method which comprises:

a. spray drying a slurry into microspheres, with said microspheres having an average diameter of from 20 microns to about 200 microns and a moisture content no greater than about 5 wt.%, with said slurry being comprised of water and catalyst source constituents of the oxides of iron, potassium, and chromium, and with said slurry having a water content of from about 20 wt.% to about 70 wt.%.

b. forming a substantially cylindrically shaped tablet from a preselected amount of said microspheres by subjecting these microspheres to a compressive pressure of at least about 22,000 psi, said tablet having a diameter of from about ⅛ inch to about ½ inch; and c. calcining the tablet at a temperature of at least 500° C.

4. A catalyst tablet for use in the dehydrogenation of ethylbenzene to form styrene said tablet being made by the method comprising:

a. in a disk type spray dryer, spray drying a slurry to form microspheres having a diameter of from about 20 microns to about 100 microns and a moisture content no greater than about 5 wt.%, with said slurry being comprised of water and catalyst source constituents of the oxides of iron, potassium, and chromium;

b. forming a substantially cylindrically shaped catalyst tablet by subjecting a pre-selected amount of the microspheres to a compressive pressure of at least about 22,000 psi in a punch and die set suitably shaped to form tablets of cylindrical shape, said tablets having a diameter of from about ⅛" to about ½" and a length substantially the same as the diameter; and c. calcining the tablet at a temperature of at least 500° C.

5. A tablet as recited in claim 4 in which the slurry is further comprised of a catalyst source constituent of $V_2O$;hd 5.

6. A method for making a fixed-bed catalyst precursor tablet which is capable of being a useful improved, fixed-bed catalyst tablet upon further treatment, which method comprises:

a. forming microspheres by spray drying a slurry of catalyst source constituents; and b. forming the tablet by compressing a selected amount of the microspheres with a compressive pressure of at least 3,000 psi.

7. The catalyst precursor tablet made by the method of claim 6.

8. A method for making a fixed bed, non-supported dehydrogenation catalyst tablet which has improved crush strength properties over those of extruded catalyst pellets, which method, in combination comprises:

a. forming microspheres by spray drying a slurry containing catalyst source constituents;

b. forming a tablet by compressing a selected amount of the microspheres at a compressive pressure of at least 3,000 psi; and c. calcining the tablet to form the catalyst tablet having improved crush strength and catalytic performance properties.

9. The improved, fixed bed, dehydrogenation catalyst tablet made by the method of claim 8.

10. A method for making an improved, fixed-bed, non-supported, dehydrogenation, catalyst tablet which has better catalytic performance and crush strength than do catalyst pellets made by conventional methods, which method, in combination, comprises:
- a. forming microspheres from a slurry containing catalyst source constituents by spray drying the slurry;
- b. forming the tablets by subjecting a selected amount of the microspheres to a compressive pressure of at least 3,000 psi; and
- c. calcining the tablet to thereby form the improved dehydrogenation catalyst tablet.

11. The fixed-bed dehydrogenation catalyst tablet made by the method of claim 10.

12. The method of claim 10 wherein in step (b) the microspheres are subjected to a compressive pressure of greater than about 15,000 psi.

13. The catalyst tablet made by the method of claim 12.

* * * * *

UNITED STATES PATENT AND TRADEMARK OFFICE
CERTIFICATE OF CORRECTION

PATENT NO. : 4,139,497
DATED : February 13, 1979
INVENTOR(S) : William M. Castor and Pete J. Menegos It is certified that error appears in the above-identified patent and that said Letters Patent are hereby corrected as shown below:

Under OTHER PUBLICATIONS, change "Spary" to --Spray--.

Col. 12, line 39; change "$V_2O;hd5.$" to --$V_2O_5$.--.

Signed and Sealed this

Sixth Day of November 1979

[SEAL]

Attest:

RUTH C. MASON
Attesting Officer

LUTRELLE F. PARKER
Acting Commissioner of Patents and Trademarks